United States Patent [19]

Patterson et al.

[11] 4,233,244

[45] Nov. 11, 1980

[54] NOVEL TECHNIQUE FOR REACTING VINYL CYCLOHEXENE WITH NITROBENZENE IN THE PRESENCE OF A HYDROGEN-TRANSFER CATALYST

[75] Inventors: John A. Patterson, Fishkill, N.Y.; Wheeler C. Crawford, Houston; James R. Wilson, Missouri City, both of Tex.

[73] Assignee: Texaco Inc., White Plains, N.Y.

[21] Appl. No.: 943,590

[22] Filed: Sep. 18, 1978

[51] Int. Cl.$^3$ ............................................. C07C 85/11
[52] U.S. Cl. .................................. 564/423; 252/430; 252/431 R; 585/434; 585/444; 564/448; 564/494
[58] Field of Search ............... 260/580, 668 D, 669 R, 260/583 M, 563 R; 252/431 R, 430

[56] References Cited

U.S. PATENT DOCUMENTS

| | | | |
|---|---|---|---|
| B 430,157 | 2/1976 | Juguin et al. | 260/668 D |
| 3,055,949 | 9/1962 | Howk et al. | 252/431 R X |
| 3,096,385 | 7/1963 | McConnell et al. | 252/431 R X |
| 3,152,131 | 10/1964 | Heberling | 252/431 R X |
| 3,156,735 | 11/1964 | Armstrong | 260/668 D X |
| 3,354,212 | 11/1967 | Donaruma | 260/580 X |
| 3,388,004 | 6/1968 | Rosenblatt | 252/430 X |
| 3,560,459 | 2/1971 | Kennedy | 252/431 R X |
| 3,600,330 | 8/1971 | Schneble et al. | 252/430 |
| 3,634,346 | 1/1972 | McKeon | 252/431 R X |
| 3,674,884 | 7/1972 | Moritani et al. | 260/669 R X |
| 3,775,342 | 11/1973 | Kronig et al. | 252/430 |
| 3,787,462 | 1/1974 | Swodenk et al. | 252/431 R X |

FOREIGN PATENT DOCUMENTS

| | | | |
|---|---|---|---|
| 45-490 | 9/1970 | Japan | 260/580 |
| 281455 | 9/1970 | U.S.S.R. | 260/580 |

OTHER PUBLICATIONS

Kozlov et al., "Chem. Ab.", vol. 65, Ab. No. 18451h (1966).
Komratova et al., "Chem. Ab.", vol. 74, Ab. No. 41590p (1971).

*Primary Examiner*—John Doll
*Attorney, Agent, or Firm*—Carl G. Ries; Robert A. Kulason; Carl G. Seutter

[57] ABSTRACT

Vinyl cyclohexene is reacted with nitrobenzene to produce ethylbenzene, aniline, and styrene at 170° C.–360° C. in the presence of a hydrogen transfer catalyst typified by palladium acetylacetonate optionally containing cobalt acetylacetonate or copper oxide.

15 Claims, 1 Drawing Figure

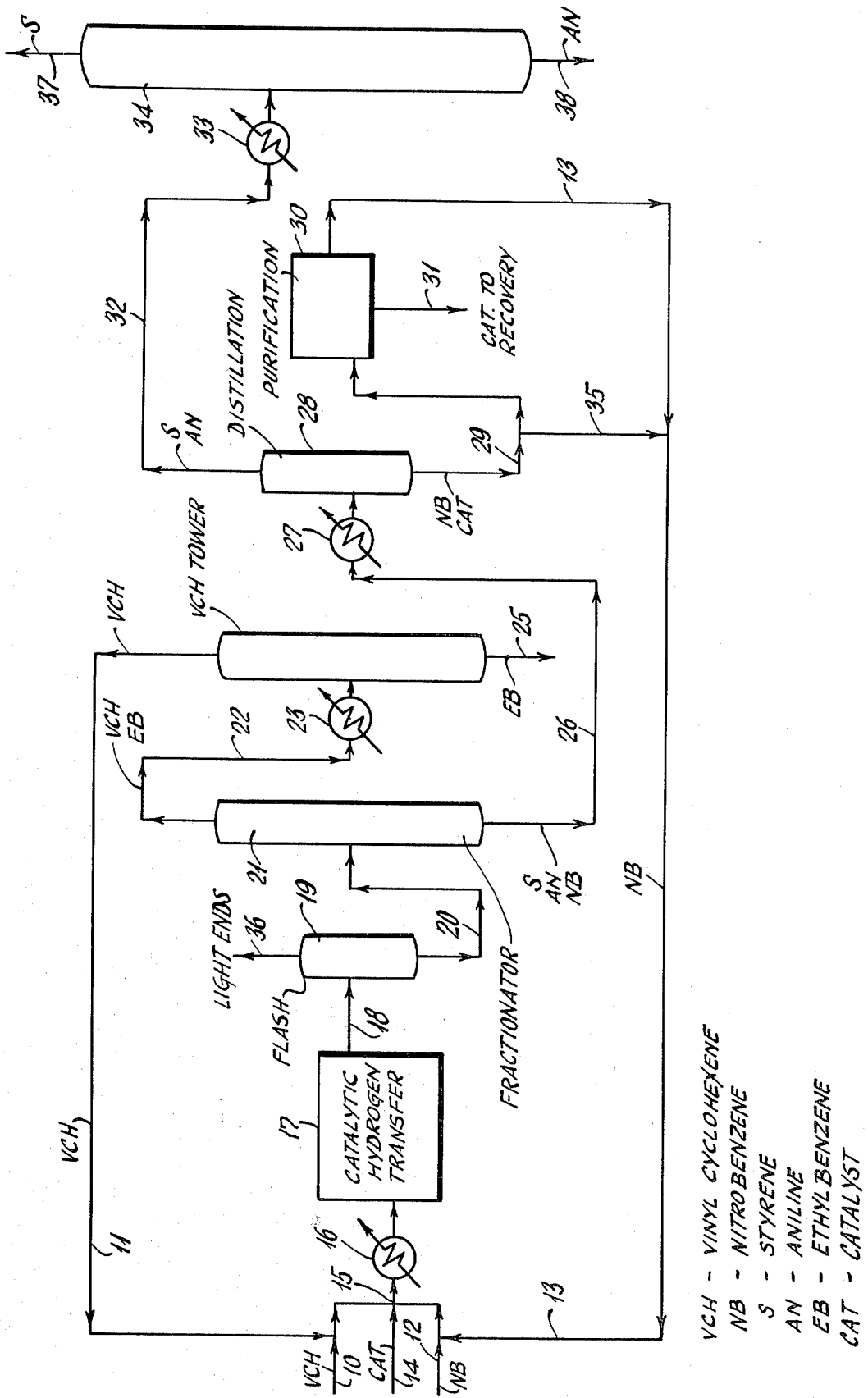

NOVEL TECHNIQUE FOR REACTING VINYL CYCLOHEXENE WITH NITROBENZENE IN THE PRESENCE OF A HYDROGEN-TRANSFER CATALYST

FIELD OF THE INVENTION

This invention relates to conversion of hydrocarbons such as 4-vinyl-1-cyclohexene to aromatic products such as ethylbenzene. More particularly it relates to the use of a catalyst to effect such conversions.

BACKGROUND OF THE INVENTION

As is well known to those skilled in the art, it is possible to prepare styrene from ethylbenzene; and there are various processes for providing ethylbenzene charge. A continuing need for increased styrene production may result in increased demand for ethylbenzene. Simultaneously it is found that decreased use of butadiene in rubber compositions results in over-supply of this material; and thus there is a source of raw material which may readily be converted (by well known processes for dimerization) to vinyl cyclohexene.

It is known (Bin Din et al, Synthesis 1978 pages 23–24) that nitro compounds may be reduced to amines in the presence of hot liquid paraffin at 360°–390° C.

SUMMARY OF THE INVENTION

In accordance with certain of its aspects, the novel method of this invention may comprise passing a charge stream containing vinyl cyclohexene and R'NO$_2$ into contact with a catalytic amount of, as catalyst, an acetylacetonate of a Group VIII metal, thereby forming product stream containing R'NH$_2$ wherein R' is alkyl, cycloalkyl, aralkyl, aryl or alkaryl; and recovering said product stream containing R'NH$_2$.

DESCRIPTION OF THE INVENTION

Charge hydrocarbon to the process of this invention is vinyl cyclohexene. 4-vinyl-1-cyclohexene, sometimes referred to as "butadiene dimer", may be commercially available or it may be prepared by dimerization of butadiene by well known processes typified by that set forth at U.S. Pat. No. 2,544,808 to A. E. Staley, or *The Chemistry of Petrochemicals* by M. J. Astle (1956) page 123. Although the process of this invention may be employed to convert 2-vinyl-1-cyclohexene or 3-vinyl-1-cyclohexene to desired products, it is found that the advantages of this process may be more readily attained using, as charge, the 4-vinyl-1-cyclohexene isomer.

The charge vinyl cyclohexene may be used as recovered in impure or crude form or it may be purified. Preferably it will be free of any added stabilizers.

The process of this invention may be carried out by reacting the vinyl cyclohexene with a nitrohydrocarbon R'NO$_2$ wherein R' is a hydrocarbon moiety selected from the group consisting of alkyl, cycloalkyl, alkaryl, aryl and aralkyl.

Although it may be possible to utilize polynitro compounds such as dinitrobenzene etc. and such compounds are included in the representation R'NO$_2$, it is more preferred to use a mononitro compound.

In the above compound, R' may be a hydrocarbon radical selected from the group consisting of alkyl, cycloalkyl, aralkyl, aryl, and alkaryl including such radicals when inertly substituted. When R' is alkyl, it may typically be propyl, butyl, i-butyl, hexyls, octyls, etc. When R' is cycloalkyl, it may typically be cyclohexyl, etc. When R' is aralkyl, it may typically be benzyl, etc. When R' is aryl, it may typically be phenyl, naphthyl, etc. When R' is alkaryl, it may typically be tolyl, xylyl, etc. R' may be inertly substituted i.e., it may bear a non-reactive substituent such as alkyl, aryl, cycloalkyl, ether, halogen, nitro, etc. Typically inertly substituted R' groups may include p-chlorophenyl, 3-chloro-5-methylphenyl, etc. The preferred R' groups may be aryl. R' may preferably be phenyl.

Illustrative compounds R'NO$_2$ may include:

TABLE nitrobenzene
dinitrobenzene
p-nitrotoluene
2,4-dinitrotoluene
p-nitrochlorobenzene
1-nitropropane
p-nitroanisole
1-nitro-n-octane
3-nitrophenol
nitrocyclohexane
1,2-dinitroaniline
6-nitroquinoline
4-nitrobenzonitrile
methyl 4-nitrobenzoate The most preferred of these compounds is nitrobenzene.

In practice of the process of this invention, vinyl cyclohexene is reacted with R'NO$_2$, in the presence of a hydrogen transfer catalyst at hydrogen transfer conditions. Hydrogen transfer catalysts are characterized by the ability of the catalyst system to exchange hydrogen between two molecules of different polarity. The preferred catalysts are homogeneous catalysts.

In practice of the process of this invention according to certain of its aspects, vinyl cyclohexene is reacted with nitrohydrocarbon R'NO$_2$ in the presence of catalyst, an acetylacetonate of a Group VIII metal. Group VIII metals which may be used in practice of the process of this invention include iron Fe, cobalt Co, or nickel Ni, as well as the Group VIII noble metals including ruthenium Ru, rhodium Rh, palladium Pd, osmium Os, iridium Ir, or platinum Pt. The preferred acetylacetonate is a noble metal acetylacetonate. This is preferred because of generally high selectivity and yield to both aniline and ethylbenzene. The Group VIII non-noble acetylacetonates such as cobalt acetylacetonates are less preferred. It may be desirable to use, as catalyst, more than one noble metal acetylacetonate or more than one non-noble metal acetylacetonates, preferably in more or less equimolar proportions.

In a less preferred embodiment, it is possible to use, as catalyst, a combination of a Group VIII noble metal (such as palladium) acetylacetonate with a Group VIII non-noble metal (such as cobalt) acetonylacetonate. Illustrative combinations of such acetylacetonates include:

TABLE

Palladium
Cobalt

Palladium
Nickel

Platinum

Nickel

Platinum

Cobalt

When combinations of acetylacetonates are used it is prefered to use 0–6, preferably 0–5, say one mole, of Group VIII noble metal acetylacetonate per mole of Group VIII non-noble metal acetylacetonate. Preferably for example, it may be possible to use one mole of palladium acetylacetonate and one mole of cobalt acetylacetonate.

In practice of this invention, it is possible to use, as catalyst, a combination of an acetylacetonate of a Group VIII metal supra with an oxide of a metal of Groub IB of the periodic table including copper, silver, or gold. The preferred oxides are those in the higher valence state. Most preferred oxide is cupric oxide CuO. In this embodiment, the mole ratio of IB oxide to acetylacetonate maybe 0.5–50, preferably 1–20, say 3:1. A preferred combination may contain three moles of cupric oxide per mole of palladium acetylacetonate.

The process of this invention may be carried out batchwise (in an autoclave) or continuously. The reaction conditions for continuous reaction may include the following:

TABLE

| Condition | Broad | Preferred | Typical |
| --- | --- | --- | --- |
| Temperature °C. | 170–360 | 170–200 | 200 |
| Pressure psig | 0–500 | 0–100 | 50 |
| LHSV | 0.003–6.0 | 0.006–2.0 | 1.5 |
| Mole ratio of R'NO$_2$ to vinyl cyclohexene | 0.1–1.0 | 0.33–0.67 | 0.67 |
| Mole ratio of catalyst to vinyl cyclohexene | 0.001–0.1 | 0.002–0.005 | 0.0026 |

The reaction conditions for batch reaction may include:

TABLE

| Condition | Broad | Preferred | Typical |
| --- | --- | --- | --- |
| Temperature °C. | 170–360 | 170–200 | 200 |
| Pressure psig | 0–500 | 0–100 | 50 |
| Time of Reaction hrs. | 1–20 | 2–15 | 10 |
| Mole ratio of R'NO$_2$ to vinyl cyclohexene | 0.1–1.0 | 0.3–0.7 | 0.67 |
| Mole ratio of catalyst to vinyl cyclohexene | 0.001–0.1 | 0.002–0.005 | 0.0026 |

The reaction is typically carried out in liquid phase under autogeneous pressure in the presence of the homogeneous catalysts.

During the course of the typical reaction, in liquid phase, hydrogen transfer occurs, the vinyl-cyclohexene being dehydrogenated to produce styrene and ethylbenzene; and nitrobenzene being reduced to aniline:

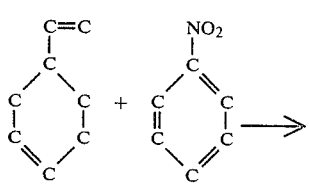

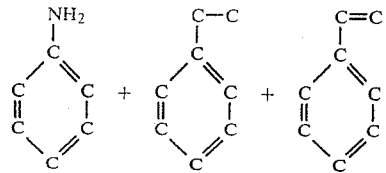

It may be desirable to carry out the reaction in the presence of a diluent-solvent which does not react under the conditions of reaction and such diluent-solvents may include hydrocarbons, preferably aromatic hydrocarbons such as benzene, xylene, toluene, etc., preferably benzene.

Reactor effluent may be characterized (in a preferred embodiment) by the presence of product ethylbenzene (EB), styrene (S), and aniline (AN) and also unreacted charge vinyl cyclohexene (VCH) and nitrobenzene (NB). Typically the yield and selectivities (in mole %) may be as follows:

TABLE

| Selectivity | Broad | Typical |
| --- | --- | --- |
| EB | 3–70 | 61 |
| S | 1–10 | 2 |
| AN | 25–60 | 52 |
| Yield | | |
| EB | 1–50 | 48 |
| S | 0–10 | 1 |
| AN | 10–30 | 23 |

It will be clear to those skilled in the art, that the yield and selectivity of a particular product may vary as the catalyst or the particular conditions of ratios, temperatures, pressures, etc. are varied.

Generally if one desires to maximize selectivity to ethylbenzene, the preferred catalysts, in decreasing order of preference may be (the numbers in parenthesis represent typical values in mole %):

TABLE

| (i) | palladium acetylacetonate | (61) |
| --- | --- | --- |
| (ii) | palladium acetylacetonate cobalt acetylacetonate | (41) |
| (iii) | palladium acetylacetonate cupric oxide | (39) |

If one desires to maximize yield of ethylbenzene, the preferred catalysts in decreasing order of preference may be:

TABLE

| (i) | palladium acetylacetonate | (48) |
| --- | --- | --- |
| (ii) | palladium acetylacetonate cobalt acetylacetonate | (26) |
| (iii) | palladium acetylacetonate cobalt acetylacetonate | (24) |

If one desires to maximize selectivity to aniline, the preferred catalysts may be:

TABLE

| (i) | palladium acetylacetonate | (52) |
| --- | --- | --- |
| (ii) | palladium acetylacetonate cupric oxide | (39) |
| (iii) | cobalt acetylacetonate | (29.4) |

If one desires to maximize yield to aniline, the preferred catalysts may be:

| | | |
|---|---|---|
| (i) | palladium acetylacetonate | (23) |
| (ii) | palladium acetylacetonate cupric oxide | (18.7) |
| (iii) | cobalt acetylacetonate | (16) |

Reaction effluent from the reaction zone is withdrwn and passed to a fractionation operation. Here there may be obtained several principle product streams:

(i) a small amount of light ends (which are produced as undesired by-products) which are withdrawn as an overhead eg from a preliminary flashing operation;

(ii) unreacted vinyl cyclohexene which may be recovered and recycled to the reaction zone;

(iii) product aniline, styrene, and ethylbenzene;

(iv) unreacted nitrobenzene bottoms which (optionally after separation from catalyst) may be recycled to the reaction zone; and (v) spent catalyst (which optionally may be recycled).

Clearly the particular recovery system will depend upon the composition of the reaction effluent and the preferred product to be recovered.

DESCRIPTION OF PREFERRED EMBODIMENTS

Practice of the novel process of this invention may be apparent from the following description of a preferred embodiment wherein, as elsewhere in this specification, all parts are parts by weight unless otherwise specifically noted. The accompanying drawing represents schematically a flow sheet of one technique whereby the process of this invention may be carried out. It will be apparent to those skilled in the art that the drawing may show major pieces of equipment, and that various pumps, valves, heat exchangers, collection drums, etc. may not be shown.

In each of Examples I-VI, there are charged to an autoclave:

(i) 16.2 parts (0.15 moles) of 4-vinyl-1-cyclohexene (butadiene dimer)

(ii) 12.3 parts (0.) moles of nitrobenzene (iii) catalyst in amount and kind as noted infra.

The reaction mixture is maintained for 10 hours at 200° C.-202° C./50 psig during which time the charge is converted to produce ethylbenzene, styrene, and aniline. The composition of the reaction mixture is tabulated infra.

The catalysts are as follows:

| Example | Catalyst | Amount parts |
|---|---|---|
| I | PdAcAc | 0.1 |
| II | PdAcAc | 0.3 |
| III | CoAcAc | 0.3 |
| IV | PdAcAc | 0.3 |
| | CoAcAc | 0.3 |
| V* | CuO | 0.3 |
| VI | CuO | 0.3 |
| | PdAcAc | 0.1 |

AcAc is an abbreviation for acetylacetonate.
*Control example

The Selectivity and Yield to ethylbenzene (EB) and to aniline (AN) and to styrne (S) are as set forth in the following Tables:

TABLE

| | Selectivity | | | Yield | | |
|---|---|---|---|---|---|---|
| Example | EB | S | AN | EB | S | AN |
| I | 3.6 | 1 | 52.33 | 1.6 | 0.5 | 13.8 |
| II | 61.5 | 0.7 | 41.3 | 48 | 0.6 | 23 |
| III | 0.5 | 2.0 | 29.4 | 0.06 | 0.2 | 16 |
| IV | 41.4 | 2.3 | 36.7 | 24 | 1.3 | 18 |
| V* | 6.3 | 0 | — | 0.3 | 0 | 14.7 |
| VI | 39.4 | 1.5 | 39.3 | 26.3 | 1 | 18.7 |

$$\text{Selectivity} = \frac{\text{Moles Product} \times 100}{\text{Moles appropriate starting material consumed}}$$

$$\text{Yield} = \frac{\text{Moles Product} \times 100}{\text{Moles appropriate starting material charged}}$$

In the case of ethylbenzene and styrene, the appropriate starting material is vinyl cyclohexene. In the case of aniline, it is nitrobenzene.

From the above, it will be apparent that:

(i) Both yield of EB and Selectivity to EB may be improved (qv Ex I-II) by increasing the amount of palladium acetylacetonate from 0.1 parts to 0.3 parts in this system;

(ii) Use of cobalt acetylacetonate rather than palladium acetylacetonate (Ex II-III) may substantially increase the relative yield of AN—eg 16/0.06 versus 23/48;

(iii) Use of a mixture of cobalt acetylacetonate and palladium acetonyl acetate (Ex IV) may give good selectivity and yield of both AN and EB—this catalyst mixture being cheaper than that of eg Ex II which gives better yield and selectivity.

(iv) Use of copper oxide alone (Ex V) is unsatisfactory;

(v) Use of copper oxide plus palladium acetylacetonate gives results generally comparable to those attained using palladium acetylacetonate alone—but at a lower catalyst cost.

Other conclusions will be readily apparent to those skilled in the art.

Results comparable to those attained in Examples I-II may be attained if the nitrocompound is:

| Example | R'NO₂ |
|---|---|
| VII | dinitrobenzene |
| VIII | p-nitrotoluene |
| IX | 2,4-dinitrotoluene |
| X | p-nitrochlorobenzene |
| XI | 1-nitropropane |
| XIII | nitrocyclohexane |

Comparable results may be attained if thecatalyst is:

| Example | | |
|---|---|---|
| XIV | Pt Ac Ac | |
| XV | Os Ac Ac | |
| XVI | Rh Ac Ac | |
| XVII | Pd Ac Ac | Pt Ac Ac |
| XVIII | Pt Ac Ac | CuO |
| XIX | Pt Ac Ac | AgO |
| XX | Pd Ac Ac | AgO |
| XXI | Pt Ac Ac | |
| | Pd Ac Ac | |
| | Cu O | |

EXAMPLE XXII

The process of this invention may be carried out continuously in accordance with the schematic flow sheet shown in the drawing.

In this embodiment, there is admitted through line 10 charge 4-vinyl-1-cyclohexene (676.4 parts) which is combined with 143.3 parts of recycle VCH from line 11. Charge nitrobenzene (284.7 parts) is added through line 12 together with 337.9 parts of recycle NB through line 13 to total 622.6 parts total charge NB. There is added through line 14, catalyst (7 parts) palladium acetylacetonate.

Charge containing VCH, NB, and catalyst is passed through line 15 and heated in heat exchanger 16 to ca. 200° C./50 psig. The mixture is passed through reaction zone 17 at LHSV of 1.5. Reaction effluent in line 18 is flashed in flash drum 19 to yield 2.3 parts of light ends withdrawn through line 36. Flashed liquid is passed through line 20 to fractionator 21 from which overhead may be withdrawn containing 143.3 parts VCH and 50.7 parts of EB. This fractionator overhead is passed through line 22 and heat exchanger 23 to VCH tower 24 from which 143.3 parts VCH is recovered and recycled through line 11. Bottoms from VCH tower 24 include 50.7 parts EB recovered through line 25.

Bottoms from fractionator 21 containing styrene, aniline, and nitrobenzene are passed through line 26 and heat exchanger 27 to distillation tower 28 from which there are recovered through line 29 bottoms containing nitrobenzene and catalyst. This stream is passed to purification operation 30 from which catalyst is passed to recovery through line 31 and 337.9 parts of nitrobenzene are recovered through line 13 and recycled to charge. Optionally nitrobenzene plus catalyst may be recycled through line 35 to the charge.

Overhead from distillation tower 28 containing 31.5 parts of styrene and 100 parts of aniline are passed through line 32 and heat exchanger 33 to rectification tower 34. Here 31.5 parts of styrene are recovered as overhead in line 37 and 100 parts of aniline are recovered as bottoms in line 38.

Although this invention has been illustrated by reference to specific embodiments, it will be apparent to those skilled in the art that various changes and modifications may be made which clearly fall within the scope of this invention.

We claim:
1. The method which comprises
    passing a charge stream containing vinyl cyclohexene and R'NO$_2$ into contact with a catalytic amount of, as catalyst, at least one acetylacetonate of a Group VIII metal, thereby forming product streams containing R'NH$_2$ wherein R' is alkyl, cycloalkyl, aralkyl, aryl or alkaryl; and
    recovering said product stream containing R'NH$_2$.
2. The method claimed in claim 1 wherein said Group VIII metal is a Group VIII noble metal.
3. The method claimed in claim 1 wherein said Group VIII metal is palladium.
4. The method claimed in claim 1 wherein said Group VIII metal is a Group VIII non-noble metal.
5. The method claimed in claim 1 wherein said Group VIII metal is cobalt.
6. The method claimed in claim 1 wherein said catalyst contains (i) an acetylacetonate of a Group VIII noble metal and (ii) an acetylacetonate of a Group VIII non-noble metal.
7. The method claimed in claim 1 wherein said catalyst contains palladium acetylacetonate and cobalt acetylacetonate.
8. The method as claimed in claim 1 which comprises
    passing a charge stream containing vinyl cyclohexene and R'NO$_2$ into contact with a catalytic amount of, as catalyst, (i) an acetylacetonate of a Group VIII metal, and (ii) 0–6 moles, per mole of acetylacetonate, of an oxide of a Group I B metal, thereby forming product stream containing R'NH$_3$; and
    recovering said product stream containing R'NH$_2$.
9. The method claimed in claim 8 wherein said oxide of a Group IB metal is CuO.
10. The method claimed in claim 8 wherein said oxide of a Group I B metal is CuO present in amount of 0–5 moles per mole of acetylacetonate.
11. The method which comprises
    passing a charge stream containing vinyl cyclohexene and nitrobenzene into contact with a catalytic amount of, as catalyst (i) palladium acetylacetonate, and (ii) 0–6 moles, per mole of palladium acetylacetonate, of copper oxide, thereby forming product stream containing aniline; and
    recovering said product stream containing aniline.
12. The method for preparing a product stream containing ethylbenzene which comprises
    passing a charge stream containing vinyl cyclohexene and nitrobenzene into contact with a catalytic amount of, as catalyst (i) one mole of palladium acetylacetonate, (ii) 0–6 moles of cobalt acetylacetonate, and (iii) 0–6 moles of copper oxide thereby forming a product stream containing ethylbenzene; and
    recovering said product stream containing ethylbenzene.
13. The method for preparing a product stream containing ethylbenzene which comprises
    passing a charge stream containing vinyl cyclohexene and nitrobenzene into contact with a catalytic amount of, as catalysts, palladium acetylacetonate thereby forming product stream containing ethyl benzene; and
    recovering said product stream containing ethylbenzene.
14. A novel catalyst which comprises
    (i) an acetylacetonate of at least one Group VIII metal; and
    (ii) an oxide of a Group I B metal.
15. A novel catalyst as claimed in claim 14 which comprises
    (i) palladium acetylacetonate;
    (ii) cobalt acetylacetonate; and
    (iii) copper oxide.

* * * * *

UNITED STATES PATENT AND TRADEMARK OFFICE
CERTIFICATE OF CORRECTION

PATENT NO. : 4,233,244

DATED : November 11, 1980

INVENTOR(S) : J. Patterson, W. Crawford, J. Wilson

It is certified that error appears in the above-identified patent and that said Letters Patent are hereby corrected as shown below:

Claim 8, line 7 (column 8, line 16) correct the formula "$R'NH_3$" to read -- $R'NH_2$ --.

Signed and Sealed this

Eighteenth Day of August 1981

[SEAL]

Attest:

Attesting Officer

GERALD J. MOSSINGHOFF

Commissioner of Patents and Trademarks